United States Patent [19]

Shin

[11] Patent Number: 5,405,605
[45] Date of Patent: Apr. 11, 1995

[54] CLEAR ANTIPERSPIRANT STICK

[75] Inventor: Chung T. Shin, Livingston, N.J.

[73] Assignee: Bristol-Myers Squibb Company, New York, N.Y.

[21] Appl. No.: 45,315

[22] Filed: Apr. 7, 1993

Related U.S. Application Data

[63] Continuation of Ser. No. 782,781, Oct. 23, 1991, abandoned, which is a continuation of Ser. No. 504,494, Apr. 4, 1990, abandoned.

[51] Int. Cl.⁶ .......................... A61K 7/34; A61K 7/36; A61K 7/38
[52] U.S. Cl. ........................................ 424/68; 424/66; 424/67
[58] Field of Search ............................ 424/68, 67, 66

[56]  References Cited
U.S. PATENT DOCUMENTS

| | | | |
|---|---|---|---|
| 3,420,932 | 1/1969 | Jones et al. | 252/47 |
| 3,630,896 | 12/1971 | Oka et al. | 252/1 |
| 4,108,977 | 8/1978 | Kenkare et al. | 424/46 |
| 4,137,306 | 1/1979 | Rubino et al. | 424/68 |
| 4,154,816 | 5/1979 | Roehl et al. | 424/68 |
| 4,183,959 | 1/1980 | Wood et al. | 424/65 |
| 4,346,079 | 8/1982 | Roehl et al. | 424/65 |
| 4,518,582 | 5/1985 | Schamper et al. | 424/66 |
| 4,719,102 | 1/1988 | Randhawa et al. | 424/68 |
| 4,720,381 | 2/1988 | Schamper et al. | 424/66 |
| 4,722,835 | 2/1988 | Schamper et al. | 424/66 |
| 4,725,430 | 2/1988 | Schamper et al. | 424/66 |
| 4,743,444 | 5/1988 | McCall | 424/65 |
| 4,781,917 | 11/1988 | Luebbe et al. | 424/65 |
| 4,816,261 | 3/1989 | Luebbe et al. | 424/65 |
| 4,822,602 | 4/1989 | Sabatelli | 424/66 |
| 4,822,603 | 4/1989 | Farris et al. | 424/66 |

FOREIGN PATENT DOCUMENTS

| | | | |
|---|---|---|---|
| 1118356 | 2/1982 | Canada | 424/68 |
| 0260030 | 8/1987 | European Pat. Off. | 424/65 |
| 0272919 | 12/1987 | European Pat. Off. | 424/68 |
| 0274267 | 12/1987 | European Pat. Off. | 424/68 |
| 0284765 | 2/1988 | European Pat. Off. | 424/65 |
| 0291334 | 5/1988 | European Pat. Off. | 424/65 |
| 0303461 | 8/1988 | European Pat. Off. | 424/66 |

Primary Examiner—C. Warren Ivy
Assistant Examiner—D. Margaret M. Mach
Attorney, Agent, or Firm—Morton S. Simon

[57] ABSTRACT

The invention provides stable, substantially anhydrous, transparent, gelled, antiperspirant sticks which are substantially free of lower monohydroxy alcohols, contain dibenzylmonsorbitol acetal as a gelling agent and are stabilized by the presence of a weakly basic, organic, nitrogen containing, stabilizing compound soluble in the composition employed to produce the stick.

11 Claims, No Drawings

CLEAR ANTIPERSPIRANT STICK

This application is a continuation application of application Ser. No. 07/782,781, filed Oct. 23, 1991, now abandoned, which is a continuation of application Ser. No. 07/504,494, filed on Apr. 4, 1990, now abandoned.

FIELD OF THE INVENTION

This invention relates to gelled antiperspirant stick compositions. More particularly, it relates to transparent, anhydrous, gelled antiperspirant compositions containing an acidic antiperspirant together with dibenzylidene monosorbitol acetal (DBMSA) as a gelling agent, stabilized by selected nitrogen containing compounds and free of aliphatic monohydroxy alcohols.

DESCRIPTION OF THE RELATED ART

Gelled antiperspirant compositions for use in preparing transparent antiperspirant sticks are known. Typically, they will contain an antiperspirant, a solvent and a gelling agent, although other ingredients such as perfumes, coloring agents and emollients may be present.

DBMSA is particularly favored as a gelling agent in transparent gelled sticks. However, DBMSA is unstable in the presence of acids and may hydrolyze to form benzaldehyde. Benzaldehyde has an almond like odor which, while not necessarily unpleasant, is generally undesirable because it indicates the hydrolytic decomposition of DBMSA which is generally accompanied by some breakdown in gel integrity.

Antiperspirant compositions contain astringent aluminum or zirconium compounds or complexes or mixtures thereof. Usually the aluminum or zirconium compounds will take the form of astringent salts.

Such compounds are of a class well known in the art. They are described, for example, in Miller and Hoag, Personal Care Products, Handbook of Nonprescription Drugs, 5th Ed., Chapter 19, pages 397–417 (American Pharmaceutical Association, 1986). Aluminum compounds are described in U.S. Pat. Nos. 3,887,692; 3,904,741 and 4,359,456; and in British Patent Specifications 2,048,229 and 1,347,950. Zirconium compounds are described in U.S. Pat. Nos. 3,679,068 and 4,120,948. All of these citations are incorporated herein by reference. Attention is also directed to the Antiperspirant OTC Monograph which discloses antiperspirant salts commonly employed in antiperspirant compositions.

Many of the commonly employed aluminum or zirconium salts are acidic and, as aforesaid, DBMSA is unstable in acidic compositions. Much effort has been expended to stabilize DBMSA in acidic compositions against hydrolytic decomposition to benzaldehyde and other products.

U.S. Pat. No. 4,719,102 describes the use of various stabilizing agents such as N-(2-hydroxyethyl) fatty ($C_8$–$C_{12}$) acid amide, magnesium sulfate, zinc acetate and hexamethylenetetramine. The last three of these compounds are also described as stabilizers in U.S. Pat. Nos. 4,518,582 and 4,720,381.

Basic metal salts such as zinc oxide, calcium acetate, magnesium oxide, calcium carbonate and calcium hydroxide are described as stabilizers in U.S. Pat. No. 4,722,835.

U.S. Pat. No. 4,725,430 describes the use of N-(2-hydroxyethyl) acetamide, alone, or combined with one or more of magnesium sulfate, zinc acetate, N-(2-hydroxyethyl) cocamide and hexamethylenetetramine as stabilizers.

Such stabilizing agents as have heretofore been discovered have not proved to be completely satisfactory principally due to discoloration and/or lack of clarity.

Other U.S. Pat. Nos. describing the use of DBMSA as a gelling agent include 4,137,306; 4,154,816; 4,720,381; 4,722,835; 4,781,917; 4,346,079; 4,822,602; 4,822,603; and 4,816,261. Foreign patents documents which relate to such compositions include Japanese Patent Publication 23170/88, which describes the use of urea as an anti-gelling agent, and European Patent Applications 0272919 and 0274267.

Many of these patents describe the use of water and lower monohydric alcohols, such as ethanol, as solvents. Such solvents are best avoided in gel stick compositions because sticks containing a high concentration of alcohol have a tendency to shrink due to evaporation of the alcohol. Additionally, it is difficult to prepare a clear antiperspirant stick due to the high melting point of DBMSA in combination with alcohol. Water and ethyl alcohol are especially unsatisfactory solvents because they are very reactive, increase the rate of hydrolysis of DBMSA and heighten the almond odor.

As will be understood from the following description, the compositions of this invention are substantially anhydrous and substantially lower monohydric alcohol free and yet, are highly transparent i.e. clear. Small amounts of water and/or alcohol can be added to the compositions of the present invention without adversely affecting stability. However, the composition becomes more and more difficult to manufacture. Thus, although operative, the inclusion of alcohol and water in the compositions of the present invention is not preferred. "Substantially free" relative to the water and lower monohydroxy or monohydric alcohol as used herein means the composition contains no more than 10%, preferably 5% or less, and most preferably 0% of the materials.

SUMMARY OF THE INVENTION

Stable, substantially anhydrous (preferably anhydrous) and substantially lower monohydric alcohol free transparent, gelled, antiperspirant compositions have now been discovered which are gelled by DBMSA, contain acidic antiperspirants, and utilize dihydric alcohols containing 3 to 6 carbon atoms as solvents. In the compositions, the DBMSA is stabilized against hydrolysis and the formation of benzaldehyde by the presence of a stabilizing amount of a selected organic base.

Organic bases useful as stabilizing agents in this invention are weakly basic nitrogen containing organic compounds which are soluble in the selected solvent system to produce a stable, transparent, deodorant stick in which the selected antiperspirant is dissolved. The preferred base will be free of offensive odors. Although the organic bases which are soluble in water and/or water/propylene glycol systems can be used in the practice of this invention, those bases which are soluble in propylene glycol are preferred. The $pKb_1$ and $pKb_2$ of the composition will be from about 3.4 to about 13.9, preferable about 3.4 to about 9.8. Strong bases which form compositions having a pH higher than 5 tend to precipitate the antipersiprant when attempts are made to employ them in the preparation of the transparent antiperspirant sticks of this invention.

The presently preferred organic bases are urea; imidazole; 2-amino-2-hydroxymethyl-1,3-propanediol (Tris buffer); 2-amino-2-methyl-1-propanol and N, N-tetrakis-2-hydroxypropyl ethylene diamine. The presently preferred organic base stabilizing agent is Tris buffer.

The compositions of the invention will be employed in the same manner as other antiperspirant compositions. They may, for example, be formed into sticks and applied to the axilla to inhibit perspiration.

DETAILED DESCRIPTION OF THE INVENTION

The antiperspirant employed in the compositions of the invention may be any of the astringent, acidic metallic salts generally utilized in such compositions provided that they are soluble in the compositions under the conditions of use. Suitable products which may be mentioned by way of example are aluminum chlorohydroxide, aluminum chloride, aluminum sesquichlorohydroxide, and zirconyl hydroxychloride. The presently preferred antiperspirant is the aluminum chlorohydrolpropylene glycol complex (ACH-Propylene Glycol Complex). The product is commercially available, for example as Rehydrol II from Reheis Chemical Company.

The amount of antiperspirant employed will be the same as normally employed in antiperspirant compositions. Such amount is described herein as an "antiperspirant quantity". Typically the amount will be, on an active basis, from about 3 to about 40%, preferably about 6 to about 25%.

In this disclosure and the appended claims, unless otherwise stated, all concentrations are in weight percent based on the total weight.

DBMSA is available commercially as Gell All-D from the New Japan Chemical Co. Ltd., Osaka or as Millilthix 925 from Milliken Chemical, Division of Milliken & Company. It is employed in an amount which will be sufficient to gel the hereinafter described compositions. Although there may be appreciable variation in the amount of DBMSA necessary to form a gel in a specific composition, it has been observed that from about 1 to about 6%, preferably about 2 to about 4% is generally sufficient.

SOLVENT

Solvents for the compositions of the invention are selected from dihydric alcohols containing from 3 to 6 carbon atoms. These include, for example, 1,3-propylene glycol; 1,2-propylene glycol; 1,3-butylene glycol; 1,4-butylene glycol; 1,5-dihydroxy pentane; and 1,6-dihydroxy hexane. The presently preferred solvent is 1,3-propylene glycol. The amount of solvent employed will be the quantity necessary to dissolve the antiperspirant in the presence of the other components of the compositions, although auxiliary solvents, other than water or lower monohydroxy alkanols, may be employed, as will be discussed below. Typically the compositions of the invention will contain from about 25% to about 90%, preferably about 40% to about 80% of the dihydric alcohol solvent.

STABILIZER

The stabilizer is an essential component of the compositions of the invention. If the instant compositions do not contain the required stabilizer, a gelled stick will not form. Organic bases which are useful as stabilizers are defined above. Stabilizers which have been found to be useful to prevent acid catalyzed hydrolytic decomposition of DBMSA in the compositions of this invention are the nitrogenous bases shown in the following table:

TABLE 1

| BASE | pKb1 | pKb2 |
| --- | --- | --- |
| Urea | 13.9 | — |
| Imidazole | 7.01 | 3.42 |
| 2-Amino-2-hydroxymethyl-1,3-propane diol (Tris buffer) | 5.92 | — |
| 2-Amino-2-methyl-1-propanol | 4.31 | — |
| N,N-Tetrakis-2-hydroxypropyl-ethylene diamine (Quadrol Polyol) | 5.64 | 9.75 |

$pKb_1$ and $pKb_2$ are calculated from the following equation:

$$pKb = 14 - pKa.$$

The protonated pKa values of the above bases are obtained from Lang's Handbook of Chemistry 13th Edition, 1985, McGraw-Hill Book Co. or from the suppliers.

Mixtures of these compounds may be used. The amount of nitrogenous base necessary to effect a useful degree of stabilization will vary with the selected stabilizer. The amount of nitrogenous base employed as a stabilizing amount should be sufficient to stabilize the DBMSA in the composition. In some compositions, as little as 0.5% may be effective, but usually from about 1 to about 20%, preferably about 1 to about 15% will be utilized. When the preferred Tris buffer is employed, the concentration range will be from about 0.5 to about 2%, preferably about 1.5 to about 1.7%. Compositions containing these quantities of stabilizers will remain transparent indefinitely under standard conditions of temperature and pressure. They may become slightly hazy at 32° F. or when subjected to freeze/thaw conditions. However, the clarity usually returns when the product is allowed to stand at room temperature for a few hours after reaching the thaw temperature.

AUXILIARY SOLVENT

N-Methyl-2-pyrrolidone (M-Pyrol) has been found to be a useful auxiliary solvent when employed in amounts up to about 20%. The clarity of the compositions has been observed to improve at concentrations up to this level, but a slight haziness appears above this concentration, especially if the compositions are held at 32° F. or subjected to freeze/thaw cycles. A special advantage to the use of N-methyl-2-pyrrolidone is that the pouring temperature of the composition is lowered. This simplifies the manufacturing process and permits the utilization of more volatile materials. The preferred amount of this auxiliary solvent is from 5 to about 15%. Propylene carbonate is another auxiliary solvent utilizable in the compositions of the present invention. It is a good solvent and helps dissolve the DBMSA. It is generally employed in amounts up to about 15%.

EMOLLIENTS/SURFACTANTS

The compositions may optionally contain one or several emollients which may additionally function as auxiliary solvents to increase clarity or as antitacking agents to prevent stickiness of the compositions after they have dried on the skin surface. Emollients are surfactants which enhance the feel of the compositions and the ease with which they can be applied. Their capacity as solvents also inhibits clouding of the compositions when exposed to decreased temperatures.

A wide variety of semipolar surfactants and emollients which are soluble or compatible with propylene glycol are known to those skilled in the art and can be utilized in the practice of this invention. Clear, liquid, semipolar emollients and surfactants are presently preferred to attain improved clarity under all temperature conditions.

Polyoxyethylene polyoxypropylene ethers of long chain fatty alcohols are especially useful. They can be represented by the formula:

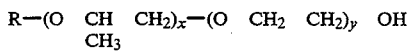

wherein R is either hydrogen or a straight or branched hydrocarbon group having from about 1 to about 18 carbon atoms, preferably from about 4 to about 18 carbon atoms. Branched chains are preferred and, of these, isostearyl is most preferred due to the clarity of products produced utilizing it, especially at low temperature conditions.

x and y are integers which are independently from about 2 to about 25, the preferred range for x being from about 2 to about 5, and for y from about 2 to about 20.

In the most preferred copolymers for use in this invention the ratio of x to x+y is equal to or less than 0.5, i.e.

$$\frac{x}{x+y} \leq 0.5$$

The semipolar components of the compositions of this invention are employed at a level of from about 3% to about 25%, preferably from about 10% to about 20%.

One class of compounds meeting the above description is disclosed in U.S. Pat. No. 4,759,924. Certain of them are commercially available under the trade names PPG-5-Ceteth 20 (available as Procetyl AWS), PPG-3-Myreth-3, PEG-20-Laurate and Polyoxamer 335.

The following Table 2 lists other semipolar materials which may be employed. They are identified by their trade names, the CTFA Dictionary Name and the commercial source of the material.

TABLE 2

| | Emollients | CTFA Name | Source |
|---|---|---|---|
| 1. | Arosurf 66-PE2 | Isosteareth-2 | Sherex |
| 2. | Arlasolve 200 | Isoceteth-20 | ICI |
| 3. | Dermol G-76 | Glycereth-7-Benzoate | Alzo |
| 4. | Brij 30 | Laureth-4 | ICI |
| 5. | Arosurf 66PE12 | PPG-3-Isosteareth-9 | Sherex |
| 6. | Cetiol HE | PEG-7-Glyceryl Cocoate | Henkel |
| 7. | Aethoxal B | PPG-5-Laureth-5 | Henkel |
| 8. | Emulgin L | PPG-2-Ceteareth-9 | Henkel |

A small quantity of non-polar emollients may optionally be included in the instant compositions. They include fatty acid esters and diesters, volatile silicones (cyclomethicone), dimethicone and hydrocarbons such as isodecane. If employed, they are used in amounts up to about 3%. At concentrations above this level, clarity of the stick may be adversely effected. Typically useful emollients of this class are disclosed in U.S. Pat. No. 4,781,917.

As used in this disclosure, the term "stable" or any variation thereof means that samples of the product, in stick form, when stored for one month at room temperature, or when stored at 104° F., will not exhibit a noticeable or objectionable benzaldehyde odor indicative of hydrolytic decomposition of DBMSA and will retain stick transparency and stick shape.

The following examples are given by way of illustration only and are not to be considered limitations of this invention, many apparent variations of which may be made without departing from the spirit or scope thereof.

EXAMPLE 1

The following components are mixed as described below to form transparent sticks of the invention:

| | % w/w |
|---|---|
| Propylene Glycol | 48.3 |
| N-Methyl-2-pyrrolidone | 10.0 |
| DBMSA | 3.0 |
| Urea | 15.0 |
| ACH-Propylene Glycol Complex[1] | 12.0 |
| Isosteareth 2 | 3.0 |
| PPG-3-Isosteareth 9 | 8.2 |
| Perfume | 0.5 |
| | 100.0 |

[1]Rehydrol II (75% aluminum chlorohydrol-25% propylene glycol)

METHOD OF PREPARATION

1. Combine propylene glycol and N-methyl-2-pyrrolidone and heat the solution to 230° F.
2. Add DBMSA at 230° F. and mix well until clear.
3. Add urea and mix until clear.
4. In a separate container, heat a solution of isosteareth-2 and PPG-3-isosteareth-9 to 210° F. Add the solution so prepared to the composition of Step 3 and mix well while the temperature rises.
5. Add the ACH-propylene glycol complex slowly and maintain the temperature at 220° F. while mixing until clear.
6. Cool to 165° F. and add the perfume. Mix well.
7. Cool to about 160° F. and then pour into containers.

It should be noted that Rehydrol II can be initially dissolved in propylene glycol and the resulting solution incorporated into the system.

EXAMPLES 2a–e

Using the procedure of Example 1, the following compositions were utilized to form clear, stable, gelled products of the invention.

| | % w/w | | | | |
|---|---|---|---|---|---|
| | 2a | 2b | 2c | 2d | 2e |
| Propylene glycol | 63.3 | 63.3 | 63.3 | 63.3 | 63.3 |
| M-Pyrol | 10.0 | 10.0 | 10.0 | 10.0 | 10.0 |
| DBMSA | 3.0 | 3.0 | 3.0 | 3.0 | 3.0 |
| Rehydrol II | 12.0 | 12.0 | 12.0 | 12.0 | 12.0 |
| Isosteareth-2 | 3.0 | 3.0 | 3.0 | 3.0 | 3.0 |
| Isoceteth 20 | 3.0 | 3.0 | 3.0 | 3.0 | 3.0 |
| FD&C Blue #1(0.1% aqueous soln.) | 0.2 | 0.2 | 0.2 | 0.2 | 0.2 |
| Fragrance | 0.5 | 0.5 | 0.5 | 0.5 | 0.5 |
| Glycereth-7-benzoate | 5.0 | — | — | — | — |
| Laureth-4 | — | 5.0 | — | — | — |
| PPG-3-Isosteareth-9 | — | — | 5.0 | — | — |
| PPG-5-Ceteth-20 | — | — | — | 5.0 | — |
| Propylene carbonate | — | — | — | — | 5.0 |
| | 100.0 | 100.0 | 100.0 | 100.0 | 100.0 |

EXAMPLES 3a-e

The following compositions were prepared and formed into clear, gelled, stable, antiperspirant sticks of the invention, which do not contain M-Pyrol, by the procedure of Example 1, except that the perfume was added in step 6 at a temperature of about 190° F. Step 7 was also conducted at the same temperature.

|  | % w/w | | | | |
| --- | --- | --- | --- | --- | --- |
|  | 3a | 3b | 3c | 3d | 3e |
| Propylene glycol | 58.3 | 58.3 | 58.3 | 58.3 | 58.3 |
| DBMSA | 3.0 | 3.0 | 3.0 | 3.0 | 3.0 |
| Urea | 15.0 | 15.0 | 15.0 | 15.0 | 15.0 |
| Rehydrol II | 12.0 | 12.0 | 12.0 | 12.0 | 12.0 |
| Isosteareth-2 | 3.0 | 3.0 | 3.0 | 3.0 | 3.0 |
| Isoceteth-20 | 3.0 | 3.0 | 3.0 | 3.0 | 3.0 |
| FD&C Blue #1 (0.1% aqueous soln.) | 0.2 | 0.2 | 0.2 | 0.2 | 0.2 |
| Fragrance | 0.5 | 0.5 | 0.5 | 0.5 | 0.5 |
| Glycereth-7-benzoate | 5.0 | — | — | — | — |
| Laureth-4 | — | 5.0 | — | — | — |
| PPG-3-Isosteareth-9 | — | — | 5.0 | — | — |
| PPG-5-Ceteth-20 | — | — | — | 5.0 | — |
| Propylene carbonate | — | — | — | — | 5.0 |
|  | 100.0 | 100.0 | 100.0 | 100.0 | 100.0 |

EXAMPLE 4a-e

The following compositions 4a and 4b of the invention were prepared and formed into clear, stable, gelled, antiperspirant sticks using the procedure of Example 1 except that other stabilizers were used in place of urea. Compositions 4c, 4d and 4e of the invention were prepared using the procedure of Example 3 except that other stabilizers were used in place of urea.

|  | % w/w | | | | |
| --- | --- | --- | --- | --- | --- |
|  | 4a | 4b | 4c | 4d | 4e |
| Propylene glycol | 63.3 | 63.3 | 73.3 | 73.3 | 72.8 |
| M-Pyrol | 10.0 | 10.0 | — | — | — |
| DBMSA | 3.0 | 3.0 | 3.0 | 3.0 | 3.0 |
| Rehydrol II | 12.0 | 12.0 | 12.0 | 12.0 | 12.0 |
| Isosteareth 2 | 3.0 | 3.0 | 3.0 | 3.0 | 3.0 |
| PPG-3-Isosteareth-9 | 8.2 | 8.2 | 8.2 | 8.2 | 8.2 |
| Imidazole | 0.5 | — | — | — | — |
| Aminomethyl Propanol | — | 0.5 | — | — | — |
| Quadrol Polyol | — | — | 0.5 | — | — |
| Tris-Buffer | — | — | — | 0.5 | 1.0 |
|  | 100.0 | 100.0 | 100.0 | 100.0 | 100.0 |

EXAMPLES 5a-d

The following compositions were employed to form clear, stable, gelled, antiperspirant sticks of the invention without M-Pyrol in accordance with the method of Example 3.

|  | % w/w | | | |
| --- | --- | --- | --- | --- |
|  | 5a | 5b | 5c | 5d |
| Propylene Glycol | 68.3 | 68.3 | 67.3 | 66.3 |
| DBMSA | 3.0 | 3.0 | 3.0 | 3.0 |
| Rehydrol II | 12.0 | 12.0 | 12.0 | 12.0 |
| Isosteareth-2 | 3.0 | 3.0 | 3.0 | 3.0 |
| PPG-3-Isosteareth-9 | 8.2 | 8.2 | 8.2 | 8.2 |
| Perfume | — | — | 0.5 | 0.5 |
| Glycereth-7-Benzoate | 5.0 | — | 5.0 | 5.0 |
| Propylene Carbonate | — | 5.0 | — | — |
| Imidazole | 0.5 | 0.5 | — | — |
| Tris-Buffer | — | — | 1.0 | 1.0 |
| PPG-3-Myristyl Ether[1] | — | — | — | 1.0 |
| | 100.0 | 100.0 | 100.0 | 100.0 |

[1] Available as Witconol - APM

EXAMPLES 6a-c

Clear, stable, gelled, antiperspirant sticks with the following ingredients were prepared according to the method of Example 3.

| Ingredients | % w/w | | |
| --- | --- | --- | --- |
|  | Ex.6a | Ex.6b | Ex.6c |
| Propylene Glycol | 66.3 | 66.3 | 66.3 |
| DBMSA | 3.0 | 3.0 | 3.0 |
| Rehydrol II | 12.0 | 12.0 | 12.0 |
| Isosteareth-2 | 3.0 | 3.0 | 3.0 |
| PPG-3-Isosteareth-9 | 8.2 | 8.2 | 8.2 |
| Tris buffer | 1.0 | 1.0 | 1.0 |
| PPG-3 Myristyl Ether | 1.0 | 1.0 | 1.0 |
| Perfume | 0.5 | 0.5 | 0.5 |
| PPG-5-Ceteth-20 | 5.0 | — | — |
| PEG-7-Glyceryl Cocoate | — | 5.0 | — |
| PPG-2-Ceteareth-9 | — | — | 5.0 |
|  | 100.0 | 100.0 | 100.0 |

EXAMPLE 7

Using the method of Example 3 clear, stable, gelled, antiperspirant sticks were prepared with the following ingredients:

|  | % w/w |
| --- | --- |
| Propylene Glycol | 64.60 |
| Rehydrol II | 12.00 |
| Tris Buffer | 1.50 |
| DBMSA | 3.00 |
| Isosteareth-2 | 3.00 |
| PPG-3-Isosteareth-9 | 8.20 |
| PEG-7-Glyceryl cocoate | 5.00 |
| PPG-5-Laureth-5 | 1.00 |
| PPG-3-Myristyl Ether | 1.00 |
| Color FDC Blue #1(0.1% Aqueous Soln.) | 0.20 |
| Perfume | 0.50 |
|  | 100.0 |

I claim:

1. A stable, substantially anhydrous, transparent, gelled antiperspirant composition substantially free of lower monohydroxy alcohol and comprising by weight, based on total weight of the composition:
   a. an antiperspirant effective amount of an acidic antiperspirant soluble in the composition;
   b. about 25% to about 90% of a dihyrdic alcohol solvent containing 3 to 6 carbon atoms;
   c. an amount of dibenzylmonosorbital acetal sufficient to gel the composition;
   d. 0 to 20% of N-methyl-2-pyrrolidone;
   e. 0 to 30% of an emollient; and
   f. about 0.5% to about 20% of a weakly basic organic nitrogen containing stabilizing compound which is soluble in the composition and has a pKb of from about 3.4 to 13.9, the amount of the stabilizing compound present being sufficient to render the composition stable, the stabilizing compound being selected from the group consisting of urea, imidazole, 2-amino-2-hydroxymethyl-1,3-propanediol, 2-amino-2-methyl-1-propanol and N,N-tetrakis-2-hydroxypropyl-ethylene diamine.

2. A composition as in claim 1, wherein the stabilizing compound is selected from the group consisting of, imidazole, 2-amino-2-hydroxymethyl-1,3-propanediol, 2-amino-2-methyl-1-propanol and N,N-tetrakis-2-hydroxypropyl-ethylene diamine.

3. The composition as in claim 2, wherein the stabilizing compound is 2-amino-2-hydroxymethyl-1,3-propane diol, and such compound is present in an amount of from about 0.5% to about 2%.

4. The composition as in claim 2, wherein the emollient is represented by the formula:

$$R-(OCHCH_2)_x-(OCH_2CH_2)_yOH$$
$$|$$
$$CH_3$$

wherein R is hydrogen or a straight or branched hydrocarbon group containing from 1 to 18 carbon atoms, x and y are integers which are independently from about 2 to about 25.

5. The composition as in claim 4, wherein x is from about 2 to about 5, and y is from about 2 to about 20.

6. A composition of claim 4, wherein the value of

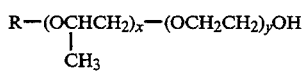

is less than or equal to 0.5.

7. The composition of claim 4, wherein R is a branched hydrocarbon group.

8. The composition of claim 4, wherein R is isostearyl.

9. The composition of claim 1, containing from about 3% to about 20% of the emollient.

10. The composition of claim 1 containing from about 3% to about 20% of an emollient selected from the group consisting of isosteareth 2, PPG-3-isosteareth-9 and PEG-7-glyceryl cocoate.

11. The composition as in claim 1, 2, 3, 4, 5, 6, 7, 8, 9 or 10 wherein the dihydric alcohol solvent is 1,3-propylene glycol.

* * * * *